United States Patent [19]

Molko et al.

[11] Patent Number: 5,179,200
[45] Date of Patent: Jan. 12, 1993

[54] N4-(3-PHENYLPROPRIONYL)-2'-DEOXYCYTIDINE

[75] Inventors: Didier Molko, Tullins-Fures; André Roget, Fontaine; Jean-Claude Schulhof, Saint Ismier; Robert Teoule, Grenoble, all of France

[73] Assignee: Commissariat a l'Energie Atomique, Paris, France

[21] Appl. No.: 255,021

[22] Filed: Oct. 7, 1988

[30] Foreign Application Priority Data

Oct. 8, 1987 [FR] France ................. 87 13911

[51] Int. Cl.$^5$ ................. C07H 19/073; C07H 21/04; C07H 21/02
[52] U.S. Cl. ................. 536/26.8; 536/28.51
[58] Field of Search ................. 536/23, 27

[56] References Cited

U.S. PATENT DOCUMENTS 4,458,066  7/1984  Caruthers ................. 536/27
4,980,460  12/1990  Molko et al. ................. 536/23

FOREIGN PATENT DOCUMENTS 0090789  3/1983  European Pat. Off. .

OTHER PUBLICATIONS

Wu et al. (1989) Nucleic Acids Research, vol. 17, No. 9, pp. 3501–3517.
Methods in Enzymology, vol. 65, Sequencing with Base-Specific Chemical Cleavages, pp. 499–560.
Nucleic Acids Research, vol. 5, No. 7, Juky 1978, The Degradation of DNA by Hydrazine: Identification of 3-Ureidopyrazole as a Product . . . .
Biochim. Biophys. Acta, 174 (1969) 591–603, The Degradation of DNA by Hydrazine: A Critical Study of the Suitability of the Reaction for the . . . .
Tetrahedron Letters, vol. 29, No. 34, pp. 4249–4252, 1988 N-Phenoxyacetylated Guanosine and Adenosine Phosphoramidites in the Solid . . . .
Nucleic Acids Research, vol. 17, No. 9, 1989, Prevention of Chain Cleavage in the Chemical Synthesis of 2'Silyated . . . .
Chemistry Letters, pp. 585–588, 1988, The Chemical Society of Japan, A New Deprotection Method for Levulinyl Protecting Groups Under . . .
Tetrahedron Letters, vol. 23, No. 26, pp. 2615–2618, 1982, K. K. Ogilivie et al., "N–Levulination of Nucleosides".
Tetrahedron Letters, vol. 40, No. 1, 1984, pp. 87–94, T. G. Heckler et al., "Preparation of 2'(3')-O-Acyl-pCpA Derivatives as Substrates for T4 RNA . . . ".

Primary Examiner—Johnnie R. Brown
Assistant Examiner—Gary L. Kunz
Attorney, Agent, or Firm—Oblon, Spivak, McClelland, Maier & Neustadt

[57] ABSTRACT

N4-(3-phenylproprionyl)-2'-deoxycytidine derivatives are disclosed having the following formula:

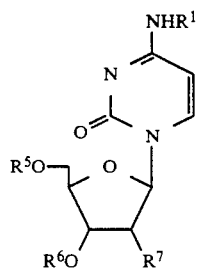

wherein $R^1$ is $-CO-CH_2-CH_2-C_6H_5$, $R^5$ is hydrogen, a trityl group or the group $-CO-CH_2-CH_2-C_6H_5$, $R^6$ is selected from the group consisting of hydrogen, $-CO-CH_2-CH_2-C_6H_5$,

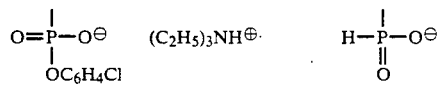

and

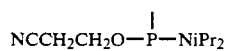

and $R^7$ is hydrogen or OH.

These derivatives are useful in oligonucleotide synthesis because the 3-phenyl-proprionyl blocking group can be removed rapidly by ammonia.

8 Claims, No Drawings

N4-(3-PHENYLPROPRIONYL)-2'-DEOXYCYTIDINE

DESCRIPTION

The present invention relates to novel derivatives of nucleosides and their use for the synthesis of oligonucleotides.

More specifically, it relates to derivatives of nucleosides usable more particularly for the synthesis of oligonucleotides and among the latter those which are formed from cytosine, i.e. a pyrimidine base having an exocyclic $NH_2$ group.

The synthesis of oligonucleotides consists of bonding together nucleosides by a phosphate group in order to form a DNA (deoxyribonucleic acid) chain or a RNA (ribonucleic acid) chain. The internucleotide phosphate groups connect the hydroxyl function in the 3'-position of a nucleoside to the hydroxyl function in the 5'-position of another nucleoside. Thus, during the synthesis reaction, only the 3' and 5' ends of the nucleosides are subject to action and the nucleic base (puric or pyrimidic base) used must not act during said bonding.

When the bases have exocyclic $NH_2$ groups, it is necessary to protect them during the synthesis against oligonucleotides, because the latter are too reactive and may interfere with the synthesis reactions.

This protection of the exocyclic $NH_2$ groups must comply with certain features:

it must be selective and easy to carry out, it must not introduce reactivity modifications of the other sites of the nucleoside and must be stable throughout the oligonucleotide synthesis stages and it must be subsequently eliminatable under gentle conditions without destroying the oligonucleotide which has just been synthesized.

The exocyclic $NH_2$ groups of the nucleosides have most frequently been protected in the form of amides, e.g. by means of benzoyl or anisoyl groups in the case of adenine and cytosine, as described by H. Schaller et al in J. Amer. Chem. Soc., 1963, Vol. 85, pp. 3821 to 3827 and by means of the isobutyryl group in the case of guanine as described by H. Buchi and H. Khorana in J. Mol. Biol., 1972, Vol. 72, pp. 251 to 288.

These protective groups can be eliminated at the end of the synthesis by the action of 28% ammonia for 17 hours at a temperature of 60° C., as is recommended. However, the NMR of the proton shows that under these conditions all the isobutyryl groups of the guanine are not eliminated. It is therefore preferable to extend the reaction time to 72 hours at a temperature of 60° C.

This method of eliminating the protective groups constitutes a disadvantage, because the conditions used are not sufficiently gentle to permit use with modified nucleosides, which are not very stable in the alkaline medium and such as is e.g. the case with 5,6-dihydrothymidine.

In addition, research has been carried out in connection with the possibility of using other more easily eliminatable acyl groups, which can in particular be used for the synthesis of oligonucleotides from unstable nucleosides by the methodology of synthesis on a support. The latter consists of fixing the first nucleoside of the chain to a support, generally made from silica and then successively carrying out the condensation cycles in order to fix the other nucleosides in the desired order to the first nucleoside. The use of more easily eliminatable acyl groups also makes it possible to obtain a better deprotection yield. This is very important because the presence of incompletely deprotected bases constitutes a disadvantage for the use of the products obtained.

During said research, it has been found that the exocyclic $NH_2$ groups of the nucleosides formed from the pyrimidine bases (cytosine) or purine bases (adenine, guanine) could be protected by an acyl group of formula:

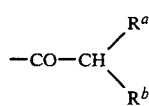

in which $R^a$ represents a hydrogen atom or an alkyl radical and $R^b$ represents a hydrogen atom, an alkyl radical, an alkoxy radical or an aryloxy radical, which made be substituted. This radical can in particular be the phenoxyacetyl group for the nucleosides formed from guanine and adenine and the isobutyryl group for nucleosides formed from cytosine. When using these new protective radicals, the deprotection operating conditions can be significantly moderated, because it is possible to obtain a complete deprotection by ammonia treatment for 2 hours at ambient temperature.

However, certain specific problems are still present for nucleosides formed from cytosine, because N-4-isobutyryl-2'-deoxycytidine has an excessive stability compared with that of the (N6-phenoxyacetyl)2'-deoxyadenosine derivatives and the (N2-phenoxyacetyl)-2'-deoxyguanosine derivative. Thus, 30 minutes are necessary for obtaining the semi-protection of the cytidine derivative, whereas 15 minutes are adequate for the 2'-deoxyguanosine derivative and only 7 minutes for the 2'-deoxyadenosine derivative.

Moreover, certain difficulties have been encountered in the preparation of the N-4-isobutyryl-2'-deoxycytidine derivative. Thus, said derivative is prepared by the reaction of isobutyryl chloride with 2'-deoxycytidine, but under these conditions a triprotected derivative of the starting nucleoside is obtained, i.e. a derivative in which the isobutyryl group protects not only the exocyclic $NH_2$ groups, but the hydroxyl functions of the deoxyribose group. Moreover, it is necessary to hydrolyse this triprotected derivative and then separate from the reaction medium and numerous salts which it contains the monoprotected derivative obtained after hydrolysis. This can be carried out by extraction with the aid of an appropriate organic solvent, but said stage lacks reproducibility, doubtless due to the respective solubilities in water of isobutyric acid and the sought derivative. The impurities left in the aqueous phase are then prejudicial to the purification of the protected nucleoside derivative by crystallization.

In addition, research has been continued with a view to finding other protective radicals of the exocyclic $NH_2$ group of 2'-deoxycytidine making it possible to obviate these disadvantages.

The present invention specifically relates to novel derivatives of nucleosides formed from cytosine, which have protective groups which are easier to eliminate than the isobutyric group and which are also easier to prepare with an adequate degree of purity.

These derivatives of nucleosides comply with the formula:

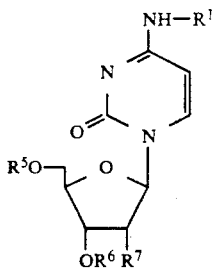 (I)

in which R¹ represents the radical of formula:

in which R² and R³, which can be the same or different, represent a hydrogen atom or an alkyl radical and R⁴ represents an aryl radical, which is unsubstituted or which is substituted by one or more groups chosen from among:

$NO_2$, CN, alkoxy, aryloxy, Cl, F,

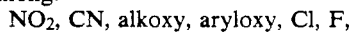

alkyl and SR with R representing an alkyl or aryl radical, R⁵ represents a hydrogen atom, a radical unstable in an acid medium or the radical of formula R¹, R⁶ represents a hydrogen atom, a phosphorus radical or the radical R¹ and R⁷ represents a hydrogen atom or the OH radical (protected or unprotected).

The use according to the invention of a radical R¹ complying with the aforementioned formula makes it possible to reduce the time necessary for deprotecting the nucleoside derivative from the R¹ radical following its use for the synthesis of oligonucleotides. Moreover, with said radical R¹, it is possible to obtain the mono-protected derivative of 2'-deoxycytidine under good conditions, with a high degree of purity and a yield exceeding 70%.

Thus, in said radical R¹, the presence of the substituents R², R³ and R⁴ makes it possible to increase the solubility difference between the nucleoside protected on the exocylic $NH_2$ group and the carbonic acid corresponding to the radical R¹. It is consequently more easily possible to extract the carboxylic acid by an ethereal phase, whilst the protected nucleoside remains sufficiently polar to be maintained in an aqueous phase.

Moreover, the presence of the substituents R², R³ and R⁴ in the beta position of the carbonyl function corresponds to a distance between the active centre and the substitution which is sufficiently large to limit the increase in the hydrolysis rate and thus prevent the nucleoside derivative from being too unstable. Thus, when they are protected by the same protective radicals, the 2'-deoxycytidine derivatives are deprotected 20 to 50 times more rapidly than their purine homologs. In the invention, the substituents and their positioning are chosen in such a way as to reduce the deprotection period of the nucleoside and to make it comparable to those necessary for deprotecting other derivatives of nucleosides such as N6-(phenoxyacetyl)-2'-deoxyadenosine.

Thus, the invention makes it possible to rapidly obtain the protected derivative with a yield exceeding 70% and the semi-deprotection time of the nucleoside derivative according to the invention, under standard conditions, can be 8 minutes, i.e. a value close to that obtained under the same conditions for N6-(phenoxyacetyl)-2'-deoxyadenosine (7 min) and N2-phenoxyacetyl-2'-deoxyguanosine (15 min). Thus, there is a significant improvement compared with the 30 minutes necessary previously with N4-isobutyryl-2'-deoxycytidine.

In the R¹ radical of the nucleoside derivative according to the invention, R² and R³ can represent a hydrogen atom or an alkyl radical and R⁴ is an optionally substituted aryl radical. The alkyl radicals which can be used can be branched or straight-chain and generally have 1 to 4 carbon atoms.

The aryl radical used is in particular the phenyl radical, but it is also possible to use any other radical derived from a nucleus by elimination of a hydrogen atom, e.g. the naphthyl, anthracenyl and similar radicals. This aryl radical can have one or more substituents chosen from among $NO_2$, CN, alkoxy, aryloxy, Cl, F, C(O)OR, C(O)R, $SO_2R$, S(O)R, $PO_3R_2$, alkyl and SR with R representing an alkyl or aryl radical. The alkyl radicals used as substituents can be of the same type as R² and R³. The alkoxy radicals usable as substituents generally have 1 to 4 carbon atoms and can be branched or straight-chained.

The aryl radicals used as substituents can be phenyl, naphthyl or anthracenyl radicals. Preferably, according to the invention, R¹ and R² represent a hydrogen atom and R⁴ represents the phenyl radical.

In the derivatives of nucleosides according to the invention, the radicals unstable in an acid medium which can be used for forming R⁵ are in particular radicals usable in oligonucleotide synthesis, such as:

the trityl radicals complying with the formula:

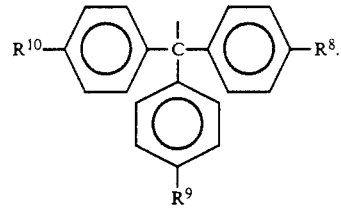

in which R⁸, R⁹ and R¹⁰, which can be the same or different, represent a hydrogen atom, an alkyl radical or an alkoxy radical, e.g. the monomethoxytrityl radical or the trityl radical of formula (V) in which R⁸ and R⁹ represent the methoxy radical and R¹⁰ represents a hydrogen atom, the pixyl radicals and 9-phenyl-xanthenyl radicals.

In the derivatives of nucleosides according to the invention, the phosphorus radicals which can be used for forming R⁶ in the compound of formula (I) are also radicals usable in oligonucleotide synthesis, such as the radical of formula:

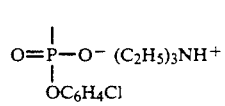 (III)

the radical of formula:

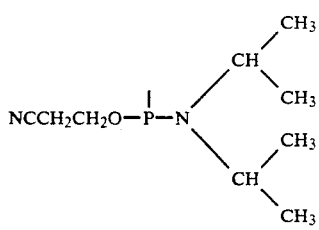 (IV)

the phosphonate radical of formula:

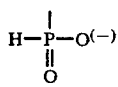

In general, the radical of formula (IV) is used.

According to the invention, when $R^7$ represents the protected OH radical, the OH protective group is constituted by groups conventionally used in the synthesis of ribonucleotides.

Thus, the derivatives of nucleosides according to the invention are the products of the union 1) of a base formed by cytosine and 2) of ribose or deoxyribose, the nucleosides being modified at least on the exocyclic $NH_2$ group of the cytosine by the $R^1$ group. They can also be modified by said same group on the 3' and 5'-positions of the deoxyribose or the 2', 3' and 5'-positions of the ribose, or the 3' and 5'-positions of the ribose or deoxyribose can be modified by other groups, which are unstable $R^5$ groups for the 5'-position and the $R^6$ phosphorus group for the 3'-position of the ribose or deoxyribose.

The acyl groups of formula:

$$R^4-C(R^2R^3)-CH_2-CO-O-CO-CH_2-C(R^2R^3)-R^4-$$

used in the invention are particularly interesting for the synthesis of oligonucleotides, because they can be easily eliminated at the end of the operation, e.g. by an ammonia treatment for 2 hours at ambient temperature, which makes it possible to simultaneously free the oligonucleotide from the support on which it was synthesized, when using the method of synthesizing on a support. This time is comparable with that necessary with nucleosides protected by the group:

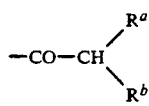

It is also possible to operate under gentle reaction conditions, because the deprotection is carried out at ambient temperature and the use of this easily eliminatable protective group makes it possible to incorporate during the synthesis of the oligonucleotides modified nucleic bases sensitive to more violent alkaline conditions, e.g. to synthesize DNA fragments carrying ligands sensitive to antibodies.

Although the invention applies to nucleosides derived from ribose and nucleosides derived from deoxyribose, it is preferably used for nucleosides derived from deoxyribose, i.e. the derivatives of formula (I) in which $R^7$ is a hydrogen atom.

The derivatives of nucleosides according to the invention can be prepared by conventional processes identical to those used for fixing benzoyl and anisoyl groups to adenine or cytosine-based nucleosides. In these processes, the starting product is the nucleoside of the cytosine which is reacted with the acid chloride of formula $R^1$Cl or the acid anhydride of formula:

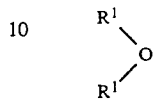

To ensure that during this reaction the acid chloride or acid anhydride does not also react with the hydroxyl groups in the 3' and 5'-positions of the ribose or deoxyribose, these hydroxyl groups are firstly protected by reacting them with an appropriate compound, which can be trimethylsilyl chloride, in an appropriate solvent such as pyridine. After the reaction of the nucleoside of the cytosine with the acid chloride $R^1$Cl or the acid anhydride $(R^1)_2O$, elimination takes place of the protective groups of the hydroxyl groups in the 3' and 5'-positions of the ribose or deoxyribose by hydrolysis, e.g. using an ammonia solution.

According to a variant of the preparation of the derivative protected by the $R^1$ group, the reaction is carried out without protecting the hydroxyl groups in the 3' and 5'-positions of the ribose or deoxyribose, then the triprotected nucleoside derivative undergoes selective hydrolysis.

It is possible to prepare derivatives of nucleosides of formula (I), in which $R^5$ represents a trityl radical of formula (II), e.g. the dimethoxytrityl group, and $R^6$ represents a hydrogen atom, by reacting the derivatives of nucleosides obtained previously with the corresponding trityl chloride in an appropriate solvent.

The derivatives of nucleosides according to formula (I), in which $R^5$ represents a dimethoxytrityl group or a methoxytrityl group and $R^6$ represents either the radical of formula (III), or the radical of formula (IV), or a radical of formula:

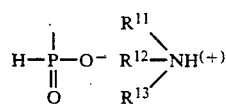

in which $R^{11}$, $R^{12}$ and $R^{13}$, which can be the same or different, are alkyl radicals, e.g. ethyl radicals and which can be prepared by conventional processes from derivatives of nucleosides of formula (I), in which $R^5$ represents a dimethoxytrityl or methoxytrityl radical and $R^6$ represents a hydrogen atom.

In order to prepare the derivatives in which $R^6$ represents, for example, the radical of formula (III), said nucleoside derivative is reacted with 4-chlorophenyl phosphoryl bistriazolidate in an appropriate solvent. The 4-chlorophenyl phosphoryl bistriazolidate can be prepared by the addition of 4-chlorophenyl dichlorophosphate to a suspension of triazole and triethylamine in dioxan.

In order to prepare derivatives in which $R^6$ represents, for example, the radical of formula (IV), it is possible to react the nucleoside derivative with β-cyanoethyl-monochloro-N,N-diisopropylaminophosphoramidite in an appropriate solvent in the presence of diisopropylethylamine or with β-cyanoethyl-bis-(N,N-diisopropylamino)-phosphite in the presence of tetrazole and diisopropylamine.

In order to prepare derivatives of nucleosides in which $R^3$ represents, for example, the radical of formula:

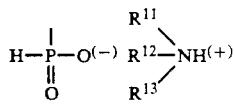

in which $R^{11}$, $R^{12}$ and $R^{13}$, which can be the same or different, are alkyl radicals, it is possible to react the nucleoside derivative with 2-chlorobenzo (5,6-a)-[1,3-dioxo-2-phosphor-4-inone] and then with a trialkyl ammonium salt, such as triethyl ammonium acetate.

The derivatives of nucleosides obtained by these three methods can be used for the synthesis of oligonucleotides either by phosphotriester synthesis in the case where $R^6$ is the radical of formula (III), or by phosphoroamidite synthesis in the case where $R^6$ is the radical of formula (IV), or by H-phosphonate synthesis in the case where $R^6$ is the radical of formula:

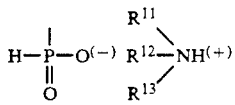

whilst also using for the assembly oligonucleotide chains of other nucleosides, e.g. those corresponding to thymidine and 2'-deoxyuridine, or nucleosides having unstable bases in an alkaline medium or other unstable nucleosides in the alkaline medium.

The inventive oligonucleotide synthesis process comprises:

1) at least one condensation cycle, in which on a nucleoside derivative or on an oligonucleotide is condensed a nucleoside derivative of formula:

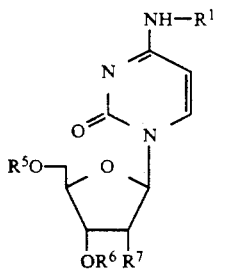 (I)

in which $R^1$ represents the radical of formula:

—CO—CH$_2$—C($R^2R^3$)—$R^4$ in which $R^2$ and $R^3$, which can be the same or different, represent a hydrogen atom or an alkyl radical, and $R^4$ represents an aryl radical which is unsubstituted or which is substituted by one or more groups chosen from among: NO$_2$, CN, alkoxy, aryloxy, Cl, F,

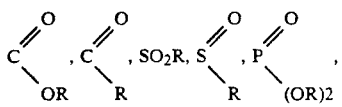

alkyl and SR with R representing an alkyl or aryl radical, $R^5$ represents a radical which is unstable in the acid medium, $R^6$ represents a phosphorus radical and $R^7$ represents a hydrogen atom and 2) a stage of eliminating the protective group or groups of formula $R^1$.

This stage can e.g. be performed by contacting the oligonucleotide with ammonia at ambient temperature.

The oligonucleotide synthesis can be carried out either by methods in solution, or by synthesis on support methods. Preference is given to the synthesis on support methods, because the latter are better adapted to the use of more unstable nucleosides without there being any loss of yield during assembly.

Thus, the nucleosides according to the invention can have interesting applications as base products for the synthesis of DNA or RNA fragments. They are also possibly suitable for incorporation into synthesis oligonucleotides of fragile modified bases, which can in particular relate to DNA gamma radiolysis products and photolysis products. The nucleosides according to the invention can also give access to novel molecules with an antiviral activity and to novel DNA probes.

The following examples concerning the preparation and use of nucleosides according to the invention are obviously given in a nonlimitative manner for the purpose of illustrating the invention.

EXAMPLE 1

Preparation of N4-(3-phenylpropionyl)-2'-deoxycytidine (compound 1)

20 mmole of deoxycytidine are dried and are then dissolved in 100 ml of anhydrous pyridine. To this solution is then added 10 ml of trimethylsilyl chloride (80 mmole) and the reaction is allowed to develop at ordinary temperature for 25 minutes. 14.6 g (50 mmole) of phenylpropionic anhydride are then added and the reaction is allowed to continue for 17 hours at 4° C.

A nucleoside has then been formed, whose alcohol functions in the 3' and 5'-positions are protected by a trimethylsilyl group and whereof the exocyclic amine function is in the form of an amide.

The 3' and 5' hydroxyl functions are freed by adding 20 ml of water and a concentrated ammonia solution until a pH of 8 is obtained. A white precipitate is then formed, which is eliminated from the solution by filtering. The solvents are then evaporated under reduced pressure. The orange coloured oily residue obtained is then taken up by 500 ml of water and said aqueous phase is washed by a mixture of ethyl ether and ethyl acetate in proportions of 80%/20% (3×500 ml). The aqueous phase is then concentrated until slight turbidity occurs and it is left at 4° C. for 17 hours. By filtering 3.8 g of N4-(3-phenylpropionyl)-2'-deoxycytidine are recovered. The mother lyes are then concentrated again and left in the cold in order to collect a new fraction of 1.3 g of product, which corresponds to an overall yield of 71%.

The product is characterized by thin film chromatography, mass spectrometry and nuclear magnetic resonance of the proton at 200 MHz. The results obtained are as follows:

Rf: 0.70 in the chloroform-methanol migration mixture (80/20), mass spectrometry (M-H): molecular peak (m/e=359-78%), nuclear magnetic resonance of the proton at 200 MHz in deuterated acetone: 8.55 ppm (d, 1H, H5), 7.44 ppm (d, 1H, H6), 6.33 ppm (t, 1H, H1'), 2.57 ppm (8 lines, 1H, H2'), 2.30 ppm (6 lines, 1H, H2''), 4.60 ppm (6 lines, 1H, H3'), 4.13 ppm (q, 1H, H4'), 3.98 ppm (q, 1H, H5'), 3.91 ppm (q, 1H, H5''), 3.20-2.90 ppm (m, 4H, propionylethyl), 7.42-7.38 ppm (m, 5H, phenyl).

EXAMPLE 2

Preparation of N4-(3-phenylpropionyl)(4,4'-dimethoxytrityl)-5'-2'-deoxycytidine (compound 2)

8 mmole of compound 1 (3 g) are dried and taken up in 50 ml of anhydrous pyridine. Cooling takes place to 0° C. and 3 g (8.8 mmole) of 4,4'-dimethoxytrityl chloride are added. The reaction is allowed to evolve at 5° C. for 17 hours and 2 ml of methanol are added. After 30 min, the solvent is expelled with the rotary evaporator and the oily residue is taken up by 300 ml of ethyl acetate, washed with 150 ml of an aqueous 5% sodium bicarbonate solution and twice with 150 ml of water. The organic phase is then dried by sodium sulphate and the mixture is fractionated on a silica gel column. Compound 2 is isolated with a yield of 40%. The physicochemical characteristics of this compound are as follows:

Rf: 0.25 in the chloroform-methanol mixture (90/10)=0.25, mass spectrometry (M-H): molecular peak m/e=660-8%, nuclear magnetic resonance of the proton at 500 MHz: 8.39 ppm (d, 1H, H5), 7.70-6.90 ppm (m, 19H, H5+aromatics), 6.31 ppm (t, 1H, H1'), 2.62 ppm (8 lines, 1H, H2'), 2.35 ppm (8 lines, 1H, H2''), 4.68 ppm (m, 1H, H3'), 4.23 ppm (q, 1H, H'4), 3.57 ppm (d, 2H, H5', H5''), 3.92 ppm (s, 6H, methoxyls).

EXAMPLE 3

Preparation of the phosphoryl derivative of compound 2 for the phosphoramidite synthesis of oligonucleotides (compound 3)

1.6 g of compound 2 are dried by addition and evaporation of 50 ml of anhydrous dichloromethane, stabilized on amylene and they are taken up with 50 ml of dichloromethane. They are added to another round-bottomed flask containing 0.170 ml of diisopropylamine, 85 mg of tetrazole and 1.05 g of bis-(diisopropylamino)-cyanoethyl phosphine in 50 ml of dichloromethane. After reacting for 3 hours at ordinary temperature, said organic phase is washed by 100 ml of aqueous 5% sodium bicarbonate solution (twice) and 100 ml of water. The solvent is then evaporated and the mixture fractionated on a silica gel column eluted by the following ternary mixture: 60% chloroform, 35% hexane and 5% triethylamine. The fractions containing the sought pure product are combined, the solvent evaporated and the colourless oily residue is taken up by 15 ml of toluene. It is poured dropwise into 250 ml of hexane previously cooled at −80° C. A precipitate of compound 3 is then collected (1.3 g, 62%), characterized by the following physicochemical data:

Rf: two spots corresponding to the two diastereoisomers 0.57 and 0.064, mass spectrometry (M+H): molecular peak m/e=8-62-1.2%, nuclear magnetic resonance at 200 MHz: the complex spectrum of such a mixture of products is very difficult to analyze. Only the signals of the following protons could be attributed with certainty: H1' 6.33 ppm (q), H3' 4.85 ppm (m), H4' 4.35 ppm (m), H5' and H5'' 3.60 ppm (m), H2'' 2.49 ppm (m), H5 8.40 ppm (dd), methoxyl 3.90 ppm (m), methyls 1.2-1.4 ppm (m).

EXAMPLE 4

This example illustrates the use of compound 3 for the synthesis of oligonucleotides having the following sequences:

5' AAT CAG ATC TAC GAA TTC T 3' (19 mer),
5' ATC AGT GCA GGG ACC GAG ATG TGC TCC AAG GAG TGT TTA TCG GCT GCT T 3' (49 mer),
5' TGC AGT CGG CTT TCG TCA CGT CCC TGG GTG TAC ACG AGG TTC CTC AGA AAT AGC CGA CGA AAG TCT ATG CTT 3' (72 mer).

In these sequences, A represents the nucleotide formed with adenine, T the nucleotide formed with thymine, C the nucleotide formed with cytosine and G the nucleotide formed with guanine. To carry out these syntheses, compound 3 is used as the synthon corresponding to cytosine. The synthons corresponding to adenine, guanine and thymine are prepared in the following way.

A) Synthon corresponding to adenine

This synthon is the phenoxyacetylated derivative of adenine complying with the following formula:

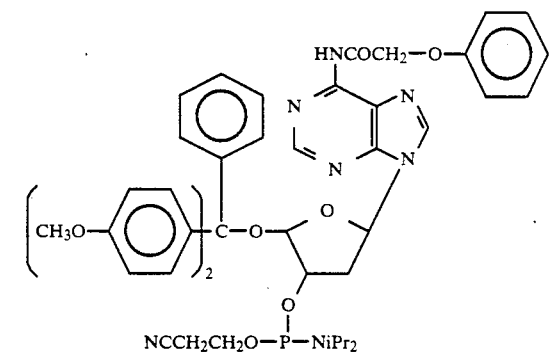

It is prepared from 2'-deoxyadenosine by carrying out the following stages:

a) Preparation of N6-(phenoxyacetyl)-2'-deoxyadenosine (compound 4)

1025 mg (4 mmole) of deoxyadenosine are dried and then dissolved in 20 ml of anhydrous distilled pyridine and then they are introduced in a round-bottomed flask placed in an ice water bath. This is followed by the slow addition of 8 equivalents of phenoxyacetic anhydride (9.5 g: 32 mmole) dissolved in 20 ml of pyridine at 0° C. The reaction is allowed to continue at ambient temperature for 90 minutes and a yellowish colouring progressively appears. In this way the triprotected nucleoside derivative is formed.

The acid anhydride excess is then destroyed at 0° C. by the addition of 3 ml of distilled water, the reaction medium then being diluted with 100 ml of chloroform. The chloroform phase is washed 4 times by means of 50 ml of an aqueous 5% sodium bicarbonate solution and the solvent is evaporated, so that a yellow residue is obtained. The latter is dissolved in 100 ml of pyridine and, after placing the solution in an ice water bath, 100 ml of 0.2N soda are added at 0° C. in order to selectively hydrolyse the 3' and 5'-positions of the adenosine in 15 min. The medium is then neutralized by means of Dowex 50W-X8 cation exchange resin in the form of pyridinium. The resin is filtered and rinsed and then the filtrate is evaporated to dryness.

This gives N6-(phenoxyacetyl)-2'-deoxyadenosine (compound 4), which is purified by silica column chromatography (diameter 4 cm and length 10 cm) using a chloroform-methanol gradient (100-0-96-4). The fractions containing the sought product are then evaporated and in this way 1010 mg of a whitish powder are obtained, which corresponds to a 65% yield.

The product is then characterized by thin film chromatography, mass spectrometry and nuclear magnetic resonance of the proton at 250 MHz. The results obtained are as follows:

Rf: 0.66 with the chloroform-methanol migration mixture (80/20 by volume), nuclear magnetic resonance of the proton at 250 MHz: $^1$H-NMR (pyridine d$_5$): 2.7-3.3, (m, 2H, H$_2$, H$_{2''}$); 4.1-4.35 (m, 2H, H$_5$H$_{5''}$); 4.6 (m, H$_{4'}$); 5.25 (m, H$_{3'}$); 5.65 (s, 2H, CH$_2$); 7.0 (m, H$_{1'}$); 6.9-7.4 (m, 5H, C$_6$H$_5$); 8.75 and 9.05 (s, H$_2$ and H$_8$).

mass spectrometry: (M+H): molecular peak (m/e: 386-16%);

phenoxyacetylated adenine (m/e: 270-66%).

b) Preparation of N6-(phenoxyacetyl)-(4,4'-dimethoxytrityl)-5'-2'-deoxyadenosine (compound 5)

2.5 mmole of compound 4 are dried by successive additions and evaporations of anhydrous pyridine, followed by taking up with 25 ml of pyridine, cooling to 0° C. and the addition of 2.75 mmole (1.1 equivalent) of 4,4'-dimethoxytrityl chloride in 25 ml of pyridine at 0° C. The reaction is allowed to continue for 17 hours at 5° C., followed by the addition of 2 ml of methanol to the reaction medium. After 30 min, the solvent is expelled with a rotary evaporator and the oily residue is taken up by 100 ml of ethyl acetate and washing takes place 3 times with 50 ml of an aqueous 5% NaHCO$_3$ solution and once with 50 ml of bidistilled water. The organic phase is then dried on sodium sulphate and concentrated. By fractionation on a silica gel column, compound 5 is isolated.

c) Preparation of the phosphoryl derivative for the phosphoroamidite synthesis of oligonucleotides (compound 6)

3 mmole of compound 5 are dried by co-evaporation of pyridine, toluene and tetrahydrofuran (THF). The residue is taken up in 15 ml of THF in the presence of 12 mmole of N,N,N-diisopropylethylamine and this is followed by the dropwise addition in 2 minutes of 6 mmole of cyanoethyl-monochloro-N,N-diisopropylamino-phosphoroamidite. After reacting for 5 minutes, the formation of a hydrochloride precipitate of the amine is observed. The reaction is allowed to continue for 35 min and the filtrate is precipitated at the end of the reaction, the filtrate is then evaporated to dryness and it is taken up in 150 ml of ethylacetate. Washing takes place by a 10% Na$_2$CO$_3$ aqueous ice solution. The organic phase is then dried on sodium sulphate and evaporated to dryness.

The compound obtained is purified by low pressure chromatography on a size B Merck "Lobar" column using for the elution a CH$_2$Cl$_2$-hexane-triethylamine mixture (70/20/10 by volume). The compound obtained is taken up by a minimum of dichloromethane or ethylacetate and is precipitated in hexane at −80° C. This gives the synthon corresponding to adenine (compound 6).

B) Synthon corresponding to guanine

This synthon is the phenoxyacetylated derivative of formula:

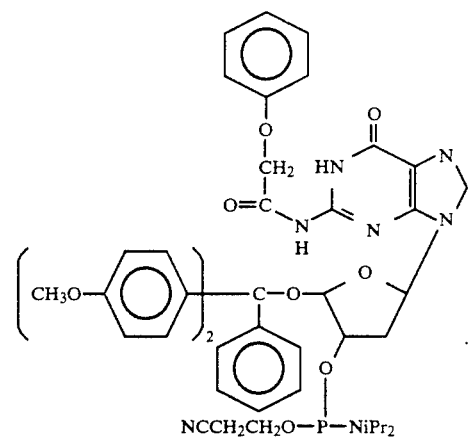

It is prepared from 2'-deoxyguanosine using the same operating procedure as for the preparation of the synthon corresponding to adenine.

C) Synthon corresponding to thymine

The latter is obtained by following the same operating procedure as hereinbefore on the basis of thymidine and without carrying out stage a).

D) Synthesis of oligonucleotides

These syntheses are carried out by means of the Applied Biosystems ABS 380 A apparatus following the protocols prescribed by the supplier and using the chemical reagents supplied by the supplier and the following quantities of synthons:

adenine synthon (compound 6): 400 mg dissolved in 4.48 ml of anhydrous acetonitrile, guanine synthon (compound 7): 400 mg dissolved in 4.64 ml of anhydrous acetonitrile, cytosine synthon (compound 3): 400 mg dissolved in 4.72 ml of anhydrous acetonitrile, thymine synthon: 400 mg dissolved in 5.28 ml of anhydrous acetonitrile.

On the apparatus are installed support cartridges grafted with thymidine (0.2 micromole) and the oligonucleotide sequences are assembled by successively carrying out condensation cycles in accordance with the protocol prescribed by the supplier.

At the end of the operation, deprotection of the oligonucleotides is carried out by subjecting the cartridge containing the oligonucleotide to the action of concentrated ammonia for 2 hours at ambient temperature. This treatment also disengages the oligonucleotide or the DNA fraction from the support. The liquid phase is then evaporated to dryness and the mixture of products then undergoes salt removal on an exclusion gel column.

Following phosphorus 32 radioactive labelling using T4-polynucleotidekinase, it is established by electrophoresis on polyacrylamide gel that the synthesized DNA fragments have the desired length.

We claim:

1. The compound having the formula:

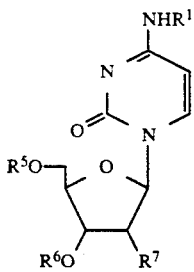

wherein $R^1$ is —CO—CH$_2$—CH$_2$—C$_6$H$_5$, $R^5$ is hydrogen, a trityl group or the group —CO—CH$_2$—CH$_2$—C$_6$H$_5$, $R^6$ is selected from the group consisting of hydrogen, —CO—CH$_2$—CH$_2$—C$_6$H$_5$,

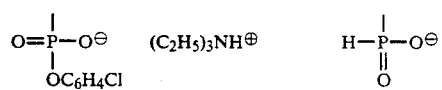

and

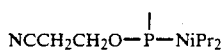

and $R^7$ is hydrogen or OH.

2. The nucleoside of claim 1, wherein $R^5$ is a trityl group of the formula:

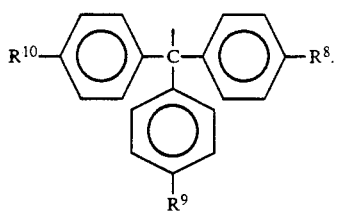

wherein $R^8$, $R^9$ and $R^{10}$, which may be the same or different, are selected from the group consisting of hydrogen, alkyl, and alkoxy, pixyl and 9-phenyl xanthenyl.

3. The nucleoside of claim 1 or 2, wherein $R^6$ is selected from the group consisting of

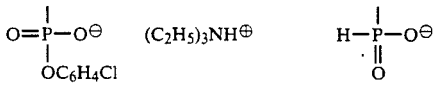

and

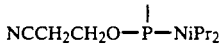

4. The nucleoside of claim 1, wherein $R^5$ and $R^6$ are hydrogen.

5. The nucleoside of claim 1, wherein $R^5$ is the group:

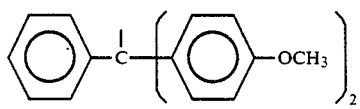

and $R^6$ is hydrogen.

6. The nucleoside of claim 1, wherein $R^7$ is hydrogen.

7. The nucleoside of claim 1, wherein $R^5$ is

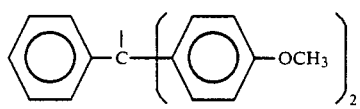

and $R^6$ is

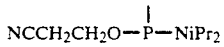

8. The nucleoside of claim 7, wherein $R^7$ is hydrogen.

* * * * *